US009259196B2

(12) United States Patent
Müller

(10) Patent No.: US 9,259,196 B2
(45) Date of Patent: Feb. 16, 2016

(54) COMPUTED TOMOGRAPHY APPARATUS FOR ODONTOLOGY

(76) Inventor: Timo Müller, Espoo (FI)

( * ) Notice: Subject to any disclaimer, the term of this patent is extended or adjusted under 35 U.S.C. 154(b) by 571 days.

(21) Appl. No.: 13/512,182

(22) PCT Filed: Nov. 23, 2010

(86) PCT No.: PCT/FI2010/050951
§ 371 (c)(1),
(2), (4) Date: Aug. 30, 2012

(87) PCT Pub. No.: WO2011/064449
PCT Pub. Date: Jun. 3, 2011

(65) Prior Publication Data
US 2012/0321035 A1 Dec. 20, 2012

(30) Foreign Application Priority Data

Nov. 25, 2009 (FI) .................................... 20090444

(51) Int. Cl.
*A61B 6/14* (2006.01)
*A61B 6/03* (2006.01)
*A61B 6/00* (2006.01)

(52) U.S. Cl.
CPC *A61B 6/14* (2013.01); *A61B 6/4441* (2013.01)

(58) Field of Classification Search
CPC .......... A61B 6/025; A61B 6/027; A61B 6/03; A61B 6/032; A61B 6/14; A61B 6/4429; A61B 6/4436; A61B 6/4441; A61B 6/501; A61B 6/54
USPC ...................... 378/4, 16, 19, 38–40
See application file for complete search history.

(56) References Cited

U.S. PATENT DOCUMENTS

| 6,069,938 | A  | * | 5/2000  | Chornenky et al. ........... 378/122 |
| 6,118,842 | A  | * | 9/2000  | Arai et al. ...................... 378/39 |
| 6,233,305 | B1 | * | 5/2001  | Muller ............................ 378/21 |
| 6,466,641 | B1 | * | 10/2002 | Virta et al. ..................... 378/38 |
| 7,486,759 | B2 |   | 2/2009  | Suzuki et al. |
| 2005/0117693 | A1 | * | 6/2005 | Miyano ............................ 378/4 |
| 2008/0137802 | A1 | * | 6/2008 | Suzuki et al. .................... 378/4 |
| 2009/0041191 | A1 |   | 2/2009 | Suzuki et al. |

FOREIGN PATENT DOCUMENTS

| JP | 2009 066305 | 4/2009 |
| WO | WO 99/17659 | 4/1999 |
| WO | WO 2006/046206 | 5/2006 |
| WO | WO 2006/097576 | 9/2006 |
| WO | WO 2006097576 A1 * | 9/2006 |
| WO | WO 2009/063974 | 5/2009 |

OTHER PUBLICATIONS

Hsieh, J., "Computed Tomography: Principles, Design, Artifacts and Recent Advantages".

* cited by examiner

*Primary Examiner* — Robert Kim
*Assistant Examiner* — David E Smith
(74) *Attorney, Agent, or Firm* — Fay Sharpe LLP

(57) ABSTRACT

The invention relates to a computed tomography apparatus designed for dental use, which includes a first arm part supporting imaging means and arranged turnable by means of an actuator, and a second arm part supporting the first arm part and arranged turnable by means of an actuator. The actuators are arranged controllable such that, during the imaging process, said first arm part does not rotate but remains in its place in relation to said second arm part and said second arm part rotates about its rotation axis.

15 Claims, 5 Drawing Sheets

COMPUTED TOMOGRAPHY APPARATUS FOR ODONTOLOGY

FIELD OF INVENTION

This invention relates to a computed tomography apparatus designed for dental use, especially to an arrangement for controlling motions of an arm construction of the imaging apparatus during an imaging process.

BACKGROUND OF INVENTION

Medical X-ray imaging has a long history. The earliest techniques were based on transilluminating the object being imaged. In transillumination, all the anatomies of the volume being imaged possibly overlapping in the direction of radiation are imaged on film on top of each other. Concerning layer imaging, i.e. a so-called tomographic imaging, on the other hand, one may get in the image being formed a desired layer of the object to become imaged more clearly by causing blurring of the other layers of the object. Depending on the imaging procedure, blurring is accomplished by changing the relative position of the imaging means and the object in a controlled manner during the imaging event either during irradiation or between individual irradiations. Especially along with advancement of computers and digital imaging, a great number of different tomographic imaging techniques and devices have been developed.

In the field of odontology, in addition to intra-oral and cephalometric imaging which are simpler as far as imaging technology is concerned as they are realized by transillumination imaging one generally uses, among other things, a so-called panoramic imaging in which, typically, a layer comprising the whole dental arch is imaged on a plane. In conventional film-based panoramic imaging, one scans over the dental arch with a narrow beam such that the centre of rotation of a turnable arm part, substantially to the opposite ends of which the imaging means have been positioned, is transferred linearly while the arm part is turned and the film moving together with the arm part is transferred through the narrow beam produced by a radiation source with a speed fulfilling the imaging condition of the imaging procedure in question. In digital panoramic imaging, the frequency at which image data is read from the sensor during an imaging scan corresponds this transfer speed of the film.

One has also begun to apply computer (or computed) tomography (CT), used earlier predominantly in hospital environment, in the field of odontology. As such, one is not able to transfer these massive and expensive CT apparatuses used in hospitals to a typical dental clinic environment, already on account of the size of the apparatuses but especially on account of their price.

Imaging-technically, several different CT technologies are known today. In CT imaging, the volume to be imaged is irradiated from different directions and, from the data thus acquired, a desired two- or three-dimensional image is reconstructed afterwards. In principle, using this kind of technology one is also able to reconstruct, among other things, a two-dimensional image outspread on a plane of a part of the dental arch or, if desired, of the whole dental arch. As far as principles of computed tomography and its different applications are concerned, a reference can be made to the literature on the art, such as to *Computed Tomography: Principles, Design, Artifacts and Recent Advantages*, Jian Hsich, SPIE PRESS, 2003, Bellingham, Wash., USA.

One form of computed tomography is the so-called cone beam CT (CBCT) in which one uses, as a distinction from the narrow beam used e.g. in panoramic imaging and conventional CT imaging, a beam substantially the size of the dimensions of the volume to be imaged and, respectively, instead of a slot sensor, a detector the size of which corresponds the size of that beam. Compared to several more conventional CT imaging technologies, by CBCT technology one is able to reach significantly smaller radiation doses and shorter imaging times.

A typical starting point in some of the CT solutions outlined and realized for odontology has been arranging the imaging means to a relatively massive, stable support construction in which the patient is positioned in a sitting position on a chair in between the imaging means, and the possible relative motions of the patient location and the imaging means, for positioning the imaging means ready for imaging a desired volume, are realized by moving the chair. On the other hand, e.g. U.S. Pat. No. 6,118,842 outlines a structure based on a traditional dental panoramic apparatus by which one is able to both turn the imaging means with respect to the centre of rotation and to change the position of the centre of rotation by means of a moving mechanism of the arm part comprising the imaging means. The dimensions of this apparatus and those of the detector used in it enable gathering information for reconstructing a volume of a certain portion of the skull but, in case one desires larger, several or e.g. adjacent volumes to be reconstructed by the apparatus, one has to repeat the imaging by first arranging the relative position of the object and the imaging means according to the new target area to be imaged.

The size of the volume one is able to image by one rotation of the imaging means can be increased with the so-called offset imaging. One known manner to realize such imaging is to arrange the imaging sensor movable before imaging to such a position with respect to the target area in which, when rotating the imaging means, at each moment of time only part of the area desired to be imaged is in the beam but, when the whole rotation has been completed, all of the partial areas of the target area have been covered at an angle range of essentially at least 180 degrees. A corresponding result is also reached by moving the position of centre of rotation of the imaging means, such as in connection with an apparatus described in U.S. Pat. No. 7,486,759, which specification is attached hereto for even more comprehensively depicting the principles of offset imaging according to prior art. However, one problem of the apparatus described in the U.S. Pat. No. 7,486,759 is the mechanically complex arrangement by which the position of the centre of rotation is arranged to be moved.

An object of the present invention and its preferable embodiments is to provide novel solutions for imaging a greater volume by one imaging than what is possible when the imaging is realized in a conventional manner by using an arm part, in which are arranged at a distance from each other a source of radiation and a receiver of image information, and when both the centre of rotation of the arm part in question and the central axis of the beam are arranged to travel and remain for the whole duration of the imaging process in the middle of the area desired to be imaged.

BRIEF DESCRIPTION OF INVENTION

The essential features of the invention are presented in the accompanying patent claims. It is substantial for the dental CT apparatus according to the invention that it comprises a set of arms and a control system which, in addition to the above-mentioned symmetrical imaging mode, enable an imaging process during which an actuator arranged to turn at least one arm part of the apparatus is controlled such that a first arm part of the set of arms supporting the imaging means does not rotate but remains in its place with respect to a second arm part of the set of arms while said second arm part rotates around its own rotation axis. When orientation of the first and the second arm part in such an arrangement is arranged other than parallel, information from an area of larger object volume may be gathered than in customary imaging according to prior art, in which the centre of rotation of the beam is stationary.

With respect to certain arrangements of prior art, the invention enables imaging a greater volume without having to arrange means to the arm part supporting the source of radiation and the imaging sensor of the apparatus e.g. for moving the imaging sensor with respect to the arm part supporting it. Then, it is also possible to avoid those problems which are caused e.g. by the asymmetrical collimation of the beam on the sensor and/or the recalibration of the imaging device when changing from the first imaging mode to the second. Also, there is no need to arrange means in the arm part supporting the imaging means to move the position of the rotation axis of the arm part and, still, the whole imaging event can be realized without moving the patient or the patient support means. The invention enables both dental panoramic imaging and imaging of volumes of several different sizes by using the same apparatus.

BRIEF DESCRIPTION OF FIGURES

Next, the invention, its preferable embodiments and their objectives and advantages will be described in more detail also with reference to the enclosed figures, of which

DETAILED DESCRIPTION OF INVENTION

Figure 1:
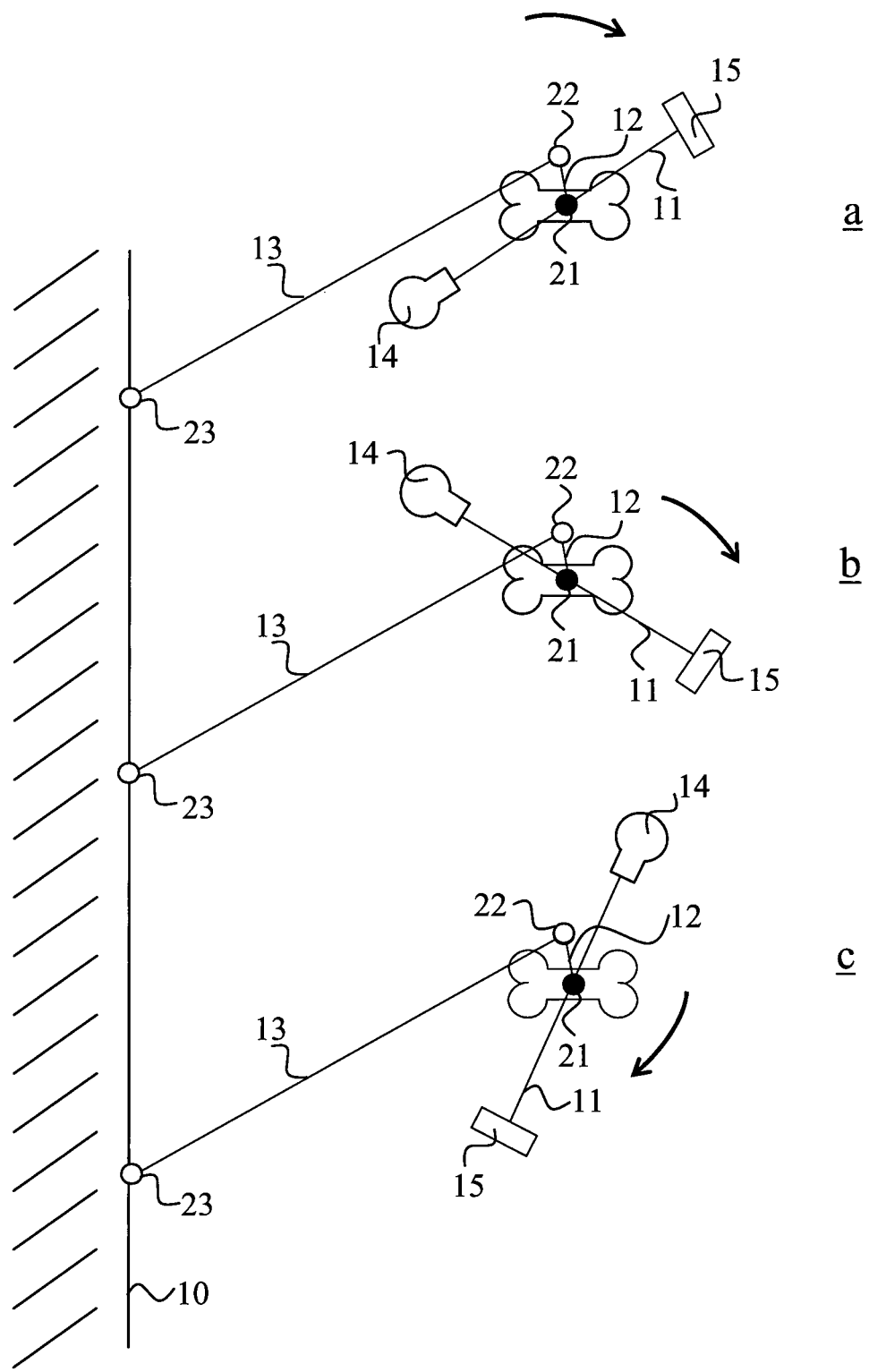
FIGS. 1a-1c show an imaging mode according to prior art in which an arm part supporting imaging means is turned around a centre of rotation of the arm part in question.

FIGS. 1a-1c show a CT imaging mode according to prior art in an apparatus which comprises a first arm part 11 comprising imaging means (a source of radiation 14 and a receiver of image information 15) and a second arm part 12 supporting said arm part 11. The first arm part 11 is arranged turnable with respect to the second arm part 12 around a first rotation axis 21 connecting said arm parts 11, 12. The source of radiation 14 and the receiver of image information 15 are arranged to the first arm part 11 at a distance from each other on opposite sides of the rotation axis 21. The apparatus includes a control system not shown in the enclosed figures and at least one actuator 31 (see FIG. 4) which is arranged to drive at least the first arm part 11 around its rotation axis 21. The arm part 12 supporting the arm part 11 supporting the imaging means 14, is further supported via a supporting arm 13 to a support structure 10.

FIGS. 1a-1c illustrate how the arm part 11 supporting the imaging means 14, 15 can be rotated by means of the actuator 31 around the rotation axis 21 being kept in place. By using a sensor 15 (receiver of image information) having a desired width and height and a beam collimated to a corresponding size as done according to prior art, it is possible to expose an object (for clarity and generality, the object to be imaged is drawn here generally as "a bone" and not skull or teeth, which is what it would in reality be when considering the present invention) positioned at the imaging device below the arm part supporting the imaging means 14, 15 from different directions and, then, to reconstruct in a manner known as such desired computed tomography images of the image information thus acquired.

In the arrangement according to FIGS. 1a-1c, the arm part 12 supporting the arm part 11 supporting the imaging means 14, 15 is arranged to its supporting arm 13 via a second rotation axis 22. This arrangement also enables such imaging modes not shown in the figures, like panoramic imaging, in which the centre of rotation 21 of the arm part 11 supporting the imaging means is moved during imaging. Furthermore, when the supporting arm 13 is also arranged turnable with respect to its own rotation axis 23, the arm part 11 supporting the imaging means 14, 15 can be positioned freely within the operating range of the set of arms 11, 12, 13, which provides versatile alternatives for realizing various imaging geometries.

FIGS. 2a-2c show an arm structure as the one shown in FIGS. 1a-1c, but now arranged to realize the imaging mode according to the invention. In this arrangement, the first arm part 11 supporting the imaging means 14, 15 is driven at a desired angle with respect to the second arm part 12 and is kept immobile during imaging with respect to the second arm part 12, while the actual motion of the imaging means 14, 15 during imaging is realized by driving the second arm part 12 about its rotation axis 22. Contrary to the case of FIGS. 1a-1c, in this arrangement the beam does not continuously cover the whole area desired to be imaged nor does the central axis of the beam generated by the source of radiation 14 continuously travel through the centre of the area desired to be imaged but asymmetrically with respect to the area to be imaged, due to which the arm construction has to be turned for the whole 360 degrees to cover the whole volume desired to be imaged. However, this asymmetrical imaging geometry ensues that, after the 360-degree rotation, information has been collected for the back projection from a greater area than in the symmetrical case according to FIGS. 1a-1c.

The size of the volume one is able to image using the imaging mode according to FIGS. 2a-2c depends on the angle between the first 11 and the second arm part 12 at which they have been arranged as non-rotatable in relation to each other for the duration of imaging. FIGS. 3a-3c show a special case of the arrangement according to FIGS. 2a-2c in which the first 11 and the second arm part 12 are parallelly oriented during imaging. Compared to the arrangement according to FIGS. 1a-1c, though, the arrangement according to FIGS. 3a-3c provides imaging of a greater volume, because the width of the beam in the area being imaged is larger in the situation according to FIGS. 3a-3c. The magnitude of this difference depends on the length of the second arm part 12, i.e., here the centre of the area being imaged is located a distance of the length of the second arm part 12 further from the source of radiation 14 than in the case of FIGS. 1a-1c.

In imaging according to FIGS. 3a-3c, the magnification ratio is different than in the imaging according to FIGS. 1a-1c in accordance with the lengths of the first 11 and the second arm part 12. However, when the size and magnification of the volume being imaged in the arrangement shown in FIGS. 3a-3c increase with respect to imaging according to FIGS. 1a-1c, they naturally would decrease in a corresponding manner if the first arm part 11 were turned for 180 degrees to another position than the one shown in FIGS. 3a-3c.

Figure 2:
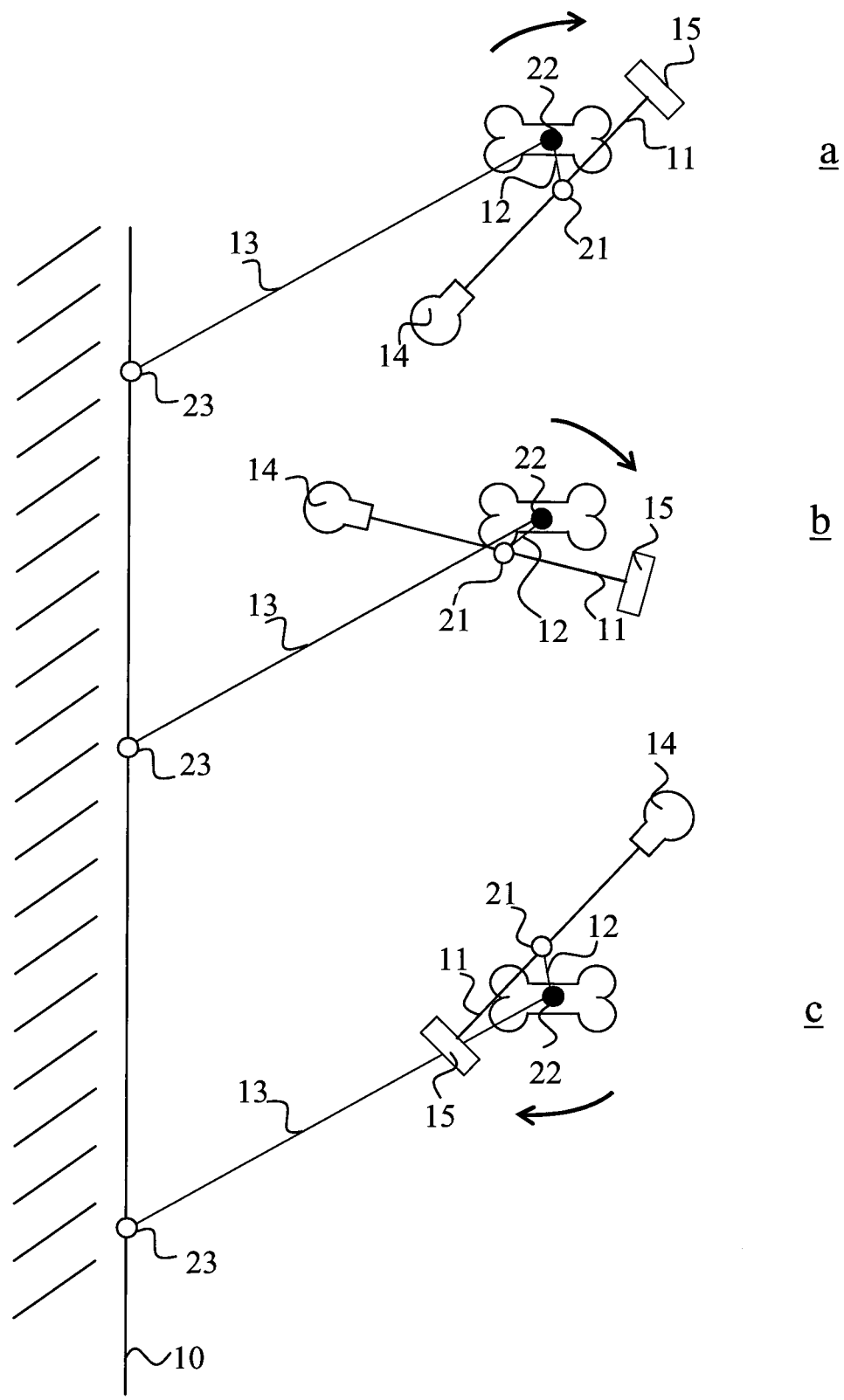
FIGS. 2a-2c show an imaging mode according to the invention in which a motion during imaging is realized by means of a rotating motion of an arm part supporting an arm part supporting imaging means.
Figure 3:
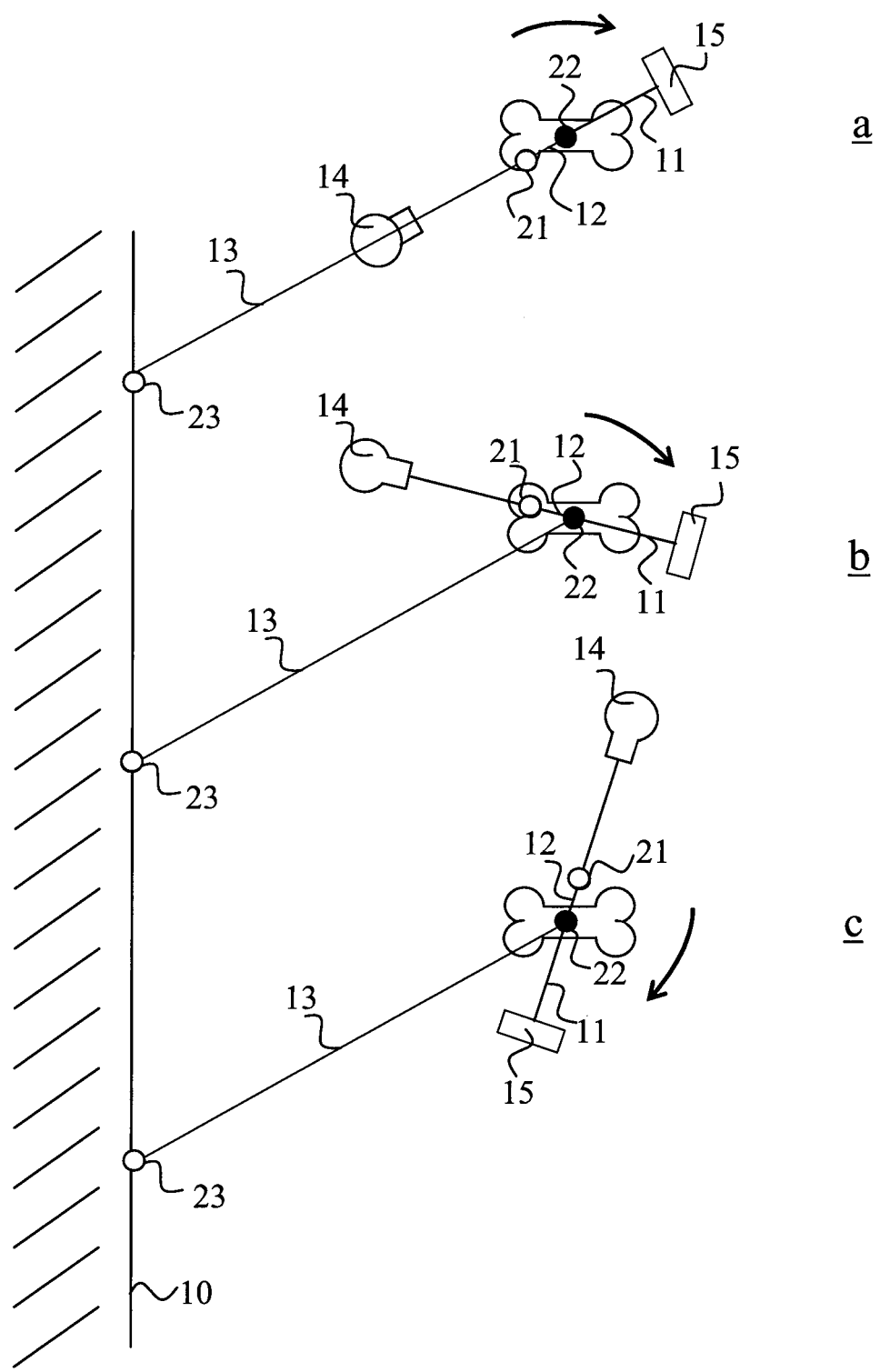
FIGS. 3a-3c show a special case of the arrangement according to FIG. 2 in which the orientation of the arm part supporting the imaging means is parallel with the arm part supporting the arm part supporting the imaging means.

One preferable embodiment of the invention, which also is not shown individually in the figures, comprises two motions done in opposite rotation directions, the first of which is done e.g. in accordance with FIG. 2 with a constant angle "alpha" between the first 11 and the second arm part 12, but now using turning angle of only 180 degrees, and the return motion of an equivalent turning angle is made otherwise similarly but now with angle "-alpha" between the arm parts in question. When operating in this manner, the rotation mechanism of the set of arms is simpler to realize as one does not have to consider the technical problems entailed by 360 degree rotation. More generally, in this imaging mode the rotation angle of the first motion and its counter-motion does not have to be particularly 180 degrees, but one is able to reach the same end-result by varying this rotation angle and, on the other hand, said angle "alpha" in a corresponding manner. The same principle is naturally also realizable with arm structures different from the one shown in FIGS. 2a-2c.

Figure 4:
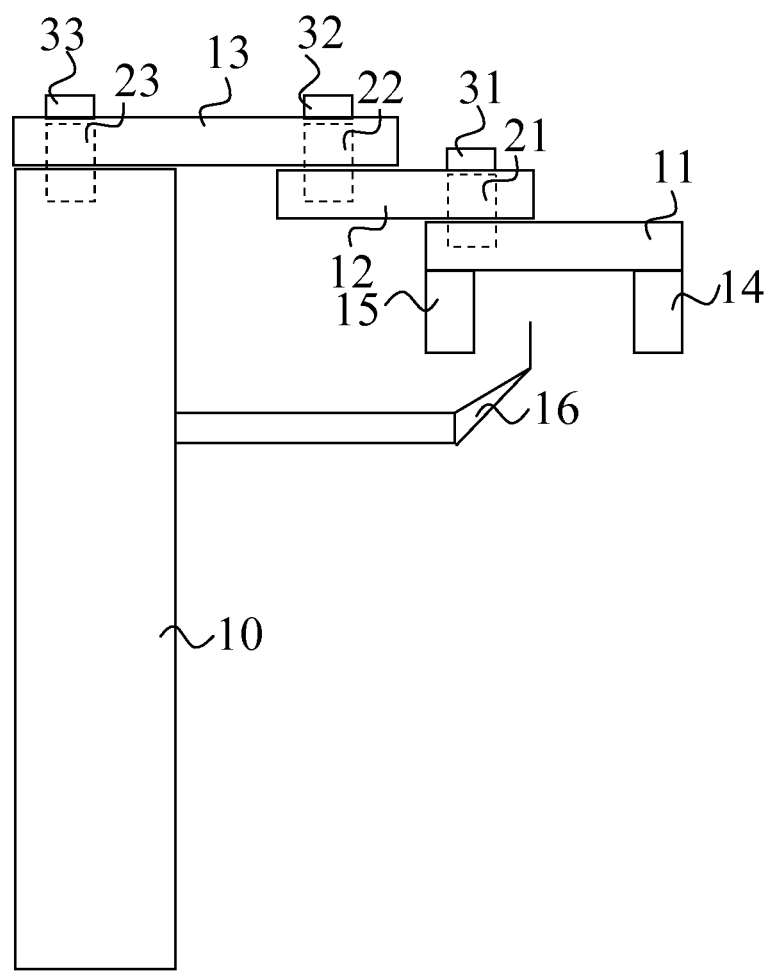
FIG. 4 shows a simplified side view of one solution for a computed tomography apparatus applicable for use in the invention.

The apparatus according to the invention can be realized as shown as simplified in FIG. 4. The support structure 10 is realized in FIG. 4 as a vertical body part 10 which supports the supporting arm 13 and the first 11 and the second arm part connected to it. The first arm part 11 supporting the imaging means 14, 15 is arranged turnable about the rotation axis 21 supported on the second arm part 12 and the second arm part 12 again turnable about the rotation axis 22 supported on the supporting arm 13. In FIG. 4, into connection with the rotation axes 21, 22 are arranged the first and the second actuator 31, 32 which can drive the first 11 and the second arm part 12 as controlled by the control system of the apparatus. According to the invention, the control system comprises control routines for realizing imagings at least in accordance with FIGS. 1a-1c and, on the other hand, with FIGS. 2a-2c. In principle, driving the first 11 and the second arm part 12 can also be realized with suitable arrangements by only one actuator. The supporting arm 13 can also be arranged turnable with respect to the support structure 10, in the arrangement according to FIG. 4, as driven by a third actuator 33. It is possible to arrange to the housing part 10 a vertical motion not shown in FIG. 4. The apparatus typically further includes a patient support means 16, which in the arrangement according to FIG. 4 is arranged in the body part 10. The supporting arm 13 can also be attached e.g. to a ceiling or wall, whereby the patient support means 16 may be arranged in some other fixed location with respect to the set of arms 11, 12, 13 of the apparatus.

In the apparatus having a vertical body part 10 according to FIG. 4, the vertical motion can be realized e.g. such that the patient support means 16 is made to move along the vertical motion of the arm construction 11, 12, 13 or such that the patient support means 16 and the arm construction 11, 12, 13 are provided with vertical freedom of movement independent of each other. With such a construction, the position of the volume being imaged may be arranged at a desired point within the operating range of the set of arms 11, 12, 13 both in horizontal and vertical direction, without moving the patient.

The imaging apparatus according to the invention can be arranged into connection with a separate computer such that the CT apparatus itself does not necessarily have to comprise means for processing the information detected by the sensor 15. The sensor 15 used in the apparatus can be e.g. a CMOS sensor or one based on so-called direct detection. It is possible to reconstruct an image of the information detected by the sensor with methods known as such, such as the so-called filtered or iterative back projection algorithms.

In the apparatus according to the invention, the desired coordinates of the rotation axes 21, 22 and orientations of the arm parts 11, 12, 13 can be arranged enterable in the control system of the apparatus via a user interface, or the apparatus can be provided with e.g. positioning lights known as such or some other corresponding arrangement via which the desired coordinates can be arranged to be transmitted to the control system automatically. The control system can also include one or more than one preset positions for the imaging means 14, 15 as well as control routines by which more than one kind of volume can be covered. In such case, a control routine can comprise control commands for driving the first 11 and the second arm part 12 to an imaging starting position which is preset or entered in the control system.

The imaging means of the CT apparatus according to the invention includes an area sensor, the so-called frame sensor, used substantially in CBCT imaging. The active surface of the sensor can be circular, rectangular or quadric, the diameter or side length of which being of the order of 10-20 cm. By arranging collimation of the beam produced by the radiation source to correspond the dimensions of such a sensor and by using SID (source-image-distance) of the order of e.g. 50-60 cm, the apparatus according to the invention can image volumes of several sizes in the area of the dental arch.

In the arrangement according to FIGS. 2a-2c, one has to rotate for 360 degrees around the area desired to be imaged whereas, when operating according to FIGS. 1a-1c and 3a-3c, even a motion of 180 degrees gives enough information for the back projection. The wider rotation angle leads to a longer imaging time and thus, among others, an increase in the load of the source of radiation. Due to this, the control system of the apparatus is preferably provided with control routines to enable, on the one hand, pulsed operation of the source of radiation 14 and, on the other hand, saving the information detected by the imaging sensor 15 and/or forwarding it periodically. Preferably, the information of the sensor is arranged readable several times a second, such as e.g. more than 10 times a second. It is preferable to synchronize the periodization of irradiation with the operation of the sensor such that the irradiation is always interrupted when information is read out from the sensor. The frequency rate is preferably arranged at least such that duration of the radiation pulse corresponds that maximum distance the beam travels in the volume being imaged which corresponds the voxel size one intends to use in the reconstruction—or said differently, duration of the radiation pulse is arranged shorter than the maximum time it can take for the beam to turn in the volume being imaged for a distance which corresponds the voxel size one intends to use in the reconstruction. Duration of the radiation pulses can also be arranged shorter, even substantially shorter than the time it takes for the imaging sensor to move during imaging for a distance of one sensor pixel. The pixel size of the imaging sensor can be arranged to be of the order of 200 μm, but even smaller as technology advances. The imaging sensor is arranged in functional connection with a computer, which computer comprises means for reconstructing a two- and/or three-dimensional image of the information detected by the sensor.

According to a preferable embodiment of the invention, instead of a customarily used constant periodic pulsing, the pulsing of the source of radiation is adjusted such that the starting frequency of pulses is kept constant but the duration of each pulse is determined based on the respective anode current at a time. This arrangement is based on compensating the technical problem of the spectrum produced by the source of radiation not typically remaining totally constant as a function of time. Thus, in this arrangement the anode current of the source of radiation is measured and, differently from arrangements according to prior art in which e.g. the acceleration voltage of the source of radiation is adjusted based on such a measurement, here duration of the pulses is controlled. The control is done such that the radiation dose produced by each pulse (mA×s) is kept constant, i.e., the pulse is terminated at the instant the integral of the current reaches a preset level. Such control is quicker than e.g. said voltage control and, regarding the imaging, it is more relevant to keep the actual dose constant than the voltage, which affects the dose indirectly. Such accurate adjustment of the source of radiation is advantageous particularly in the offset imaging according to the invention in which the imaging process is quite long as the imaging means turns for the full 360 degrees, which requires time and thus, the load for the source of radiation becomes great.

Figure 5A:
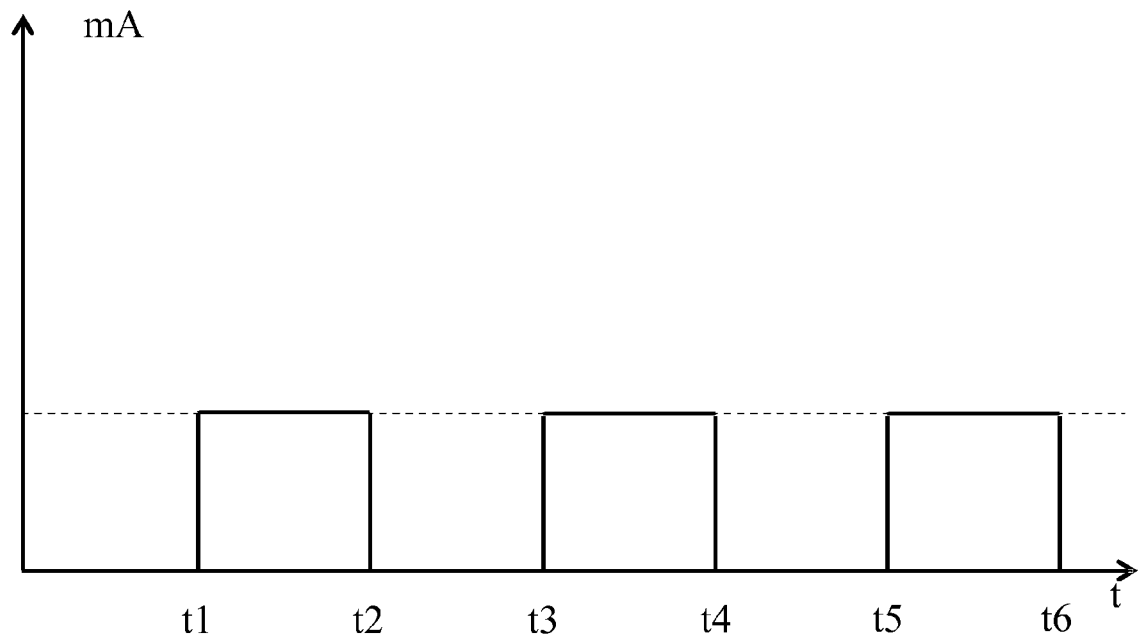
FIGS. 5a and 5b show pulsing of irradiation during asymmetrical imaging according to the invention.

The control described above is illustrated in FIGS. 5a and 5b. FIG. 5a shows a pulsed anode current as a function of time according to an ideal situation, whereby the source of radiation produces pulses of constant magnitude and duration at a constant frequency. FIG. 5b, again, shows real pulsing according to the invention in which pulses are still produced at a constant frequency but in which deviations from the set values detected in the anode current measurement are compensated by adjusting duration of the pulse longer or shorter such that the integral, as shown by the areas in FIG. 5b, remains constant.

Figure 5B:
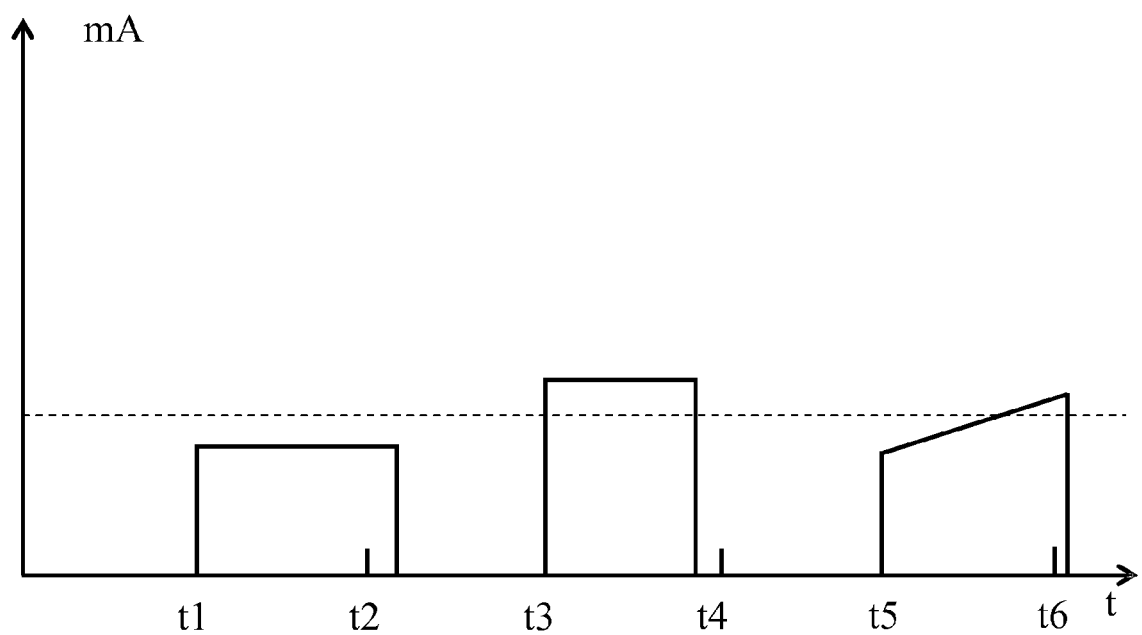

The last pulse of FIG. 5b illustrates that the anode current is not necessary constant even during individual pulses but, according to this embodiment of the invention, also a change occurring during a pulse can be compensated by cutting off the tube voltage in accordance with how the anode current varies during each pulse.

It is obvious by those skilled in the art that, especially with advancement of technology, the basic idea of the invention can be realized in many different ways, and its different embodiments are not limited to the above examples but they can vary within the scope defined by the accompanied claims. As an example, it can be noted that the term "rotation axis" used in this specification is not intended to be narrowly understood as a physical axis, but it can refer to any virtual axis providing corresponding functionality or a physical pivot, bearing or some other structure.

The invention claimed is:
1. A dental computed tomography apparatus, which includes
   a first arm part arranged turnable around a first substantially vertical rotation axis with the help of an actuator to which arm part and at a distance from each other and on the opposite sides of said rotation axis, a source of radiation and a receiver of image information have been arranged,
   a second arm part arranged turnable around a second substantially vertical rotation axis which second arm part is arranged to support said first arm part, and
   a control system for controlling one or more than one actuator driving said arm parts, the radiation source, and the receiver of image information which control system comprises a first control routine which during the imaging process controls said at least one actuator such that the first arm part rotates around said first substantially vertical rotation axis, wherein
   the control system comprises a second control routine which controls said at least one actuator of the apparatus such that, during the imaging process, for a duration of an imaging scan, said first arm part does not rotate but remains in its place in relation to said second arm part and said second arm part rotates around its rotation axis.

2. An apparatus according to claim 1, wherein said second control routine comprises a step in which, before the actual imaging process, the first arm part is driven at a desired angle with respect to the orientation of the second arm part.

3. An apparatus according to claim 1, wherein said second control routine comprises turning the second arm part about its rotation axis substantially for 360 degrees.

4. An apparatus according to claim 1, wherein said second control routine comprises a step in which, before the actual imaging process, the first arm part is driven to lie substantially parallel with said second arm part.

5. An apparatus according to claim 1, wherein said first arm part is supported by said second arm part via the rotation axis of the first arm part.

6. An apparatus according to claim 1, wherein the rotation axes of said first and second arm part are substantially parallel and/or the distance between them is constant.

7. An apparatus according to claim 1, wherein said control system comprises a control routine which includes control commands for transferring said first and second arm part to a preset starting position of imaging, or to one pre-entered in the control system.

8. An apparatus according to claim 1, wherein said receiver of image information is arranged at a distance on the order of 50-60 cm from the source of radiation.

9. An apparatus according to claim 1, wherein said imaging sensor is an area sensor which is circular, rectangular or quadric and a diameter or side length of which is of the order of 10-20 cm.

10. An apparatus according to claim 9, wherein said imaging sensor is arranged to save and/or forward the information it has received several times a second.

11. An apparatus according to claim 1, wherein said control system is arranged to control said source of radiation to produce radiation as pulsed.

12. An apparatus according to claim 11, wherein at least said second control routine comprises adjusting duration of the radiation pulses such that anode current of the source of radiation is measured and the pulse is always terminated at the point when integral of the current reaches a preset value.

13. An apparatus according to claim 11, wherein said control system is arranged to control reading of information from said imaging sensor to take place at those moments when the irradiation has been interrupted.

14. An apparatus according to any one of claim 11, wherein duration of a single radiation pulse is arranged shorter than the maximum time it may take for the beam to turn in the volume being imaged for a distance with corresponds the voxel size one intends to use in the reconstruction, or shorter or substantially shorter than the time which lapses when said imaging sensor moves during imaging a distance of one sensor pixel.

15. An apparatus according to claim 10, wherein said imaging sensor is arranged to save and/or forward the information it has received at least 10 times a second.

* * * * *